United States Patent [19]

Messing et al.

[11] 4,126,516

[45] Nov. 21, 1978

[54] METHOD FOR DISTINGUISHING GRAM POSITIVE AND GRAM NEGATIVE MICROBES

[75] Inventors: Ralph A. Messing, Horseheads; William S. Ramsey, Corning, both of N.Y.

[73] Assignee: Corning Glass Works, Corning, N.Y.

[21] Appl. No.: 745,655

[22] Filed: Nov. 29, 1976

[51] Int. Cl.$^2$ .............................................. C12K 1/06
[52] U.S. Cl. ............................................ 195/103.5 R
[58] Field of Search ............... 195/103.5 M, 103.5 R, 195/103.5 K, 127, 139

[56] References Cited

U.S. PATENT DOCUMENTS 3,165,450  1/1965  Scheidt ................................ 195/139

OTHER PUBLICATIONS

Chemical Abstracts, vol. 75, 59948s, 1975.
Biochemical Detection Methods for Bacteria and Viruses, M. A. Mitz and G. C. Blanchard, Melpar Inc., pp. 7-10, 1963.
Arch. Mikrobiol., vol. 77, pp. 118-126, 1971.

*Primary Examiner*—Lionel M. Shapiro
*Assistant Examiner*—Robert J. Warden
*Attorney, Agent, or Firm*—Clinton S. Janes, Jr.; Clarence R. Patty, Jr.; William E. Maycock

[57] ABSTRACT

Microbial culture device containing a growth medium having incorporated therein a lipophilic fluorescent material and means associated therewith for localizing and identifying the growth of colonies of an unknown microbe, and a known gram positive microbe, and/or a known gram negative microbe. The device can be used to determine whether an unknown microbe sample is gram positive or gram negative by culturing the unknown on the medium and then comparing the fluorescence of the unknown microbes with fluorescence of similarly cultured gram positive and/or gram negative microbes.

22 Claims, 5 Drawing Figures

METHOD FOR DISTINGUISHING GRAM POSITIVE AND GRAM NEGATIVE MICROBES

RELATED PATENT APPLICATION

Patent Application Ser. No. 701,894, "Microbial Medium Having Fluorescent Growth Indicator," filed July 1, 1976 now U.S. Pat. No. 4,049,499 in the names of C. A. Lepp et al. and assigned to the same assignee as this application.

BACKGROUND OF THE INVENTION

1. Field

This disclosure is concerned generally with a microbial culture device and a method of determining whether a sample of an unknown microbe can be deemed gram positive or gram negative.

2. Prior Art

All bacteria may be classified as either gram positive or gram negative depending on the staining properties of the cells. The gram stain reaction may be correlated with a large number of other properties and it is perhaps the single most important piece of information which may be communicated about a given species of bacteria. See, for example, Lammanna, C. and Mallette, M., Basic Bacteriology, 3rd Ed., Williams (1965). Wilkins, Baltimore, Maryland, pp. 162-164, (1965).

Very generally, the determination of whether a given microbe is gram positive or gram negative is performed as follows: a sample of an unknown colony is smeared on a microscope slide, a drop of water is added, and the sample is permitted to dry on the slide. The brief use of a flame causes the bacteria to stick to the slide. Then a crystal violet solution is added to the specimen, after which the specimen appears purple. This is followed by the addition of an iodine solution. After this step, the entire sample still appears purple. At this point, however, the stain of gram positive samples is immobilized within cell walls whereas the stain of gram negative remains free within the cell walls. The slide is then washed with alcohol until no more purple stain comes off with the washings. At this point, a gram positive sample, having stain immobilized in the cell walls, remains purple. A gram negative sample becomes colorless. The slide is then counterstained with safranin (red dye) after which a gram positive sample remains purple while a gram negative sample becomes red. The test is completed by washing the slide with water, drying it, and observing the specimen with a microscope to determine the specimen color.

Although the above steps themselves may appear to be relatively simple, it is known that the proper execution and interpretation of the gram stain requires considerable degrees of training and skill. Further, the test requires the availability of a high-power microscope and takes at least 5 minutes beyond sample culture time. In addition, the gram staining properties of some bacteria are dependent on the age of the culture. Also, the capacity of bacteria to grow on various selective media often correlates with the gram staining property. For example, incorporation into culture media of certain dyes, such as crystal violet or brilliant green, tends to inhibit the growth of gram positive bacteria more than that of the gram negative microbes. On the other hand, the incorporation of phenylethyl alcohol into media tends to inhibit gram negative organisms more than gram positive species. In addition to the known disadvantages associated with present methods for determining gram properties, it is known that the effects of growth inhibitors is only relative (i.e., the favored organisms are inhibited somewhat even under permissive conditions and several different inhibitory media are required to examine an organism of unknown gram properties.)

Although the exact chemical and/or physical mechanism of the gram staining procedure is not completely understood, it is known that the cell walls of gram positive and gram negative organism have significant chemical differences. For example, cell walls of gram positive microbes comprise about 90% peptidoglycan with the remaining constituents comprising teichoic acid, lipids, polysaccharides, and proteins. On the other hand, cell walls of gram negative microbes comprise about 5 to 20% peptidoglycan with the remaining constituents comprising lipids, polysaccharides, and proteins. See, for example, Brock, T. D. Biology of Microorganisms, 2nd Ed., Prentice-Hall (1974). In general, gram negative organisms have significantly more lipids in their cell walls than gram positive species.

It is known that certain lipophilic fluorescent probes such as 8-anilino-1-naphthalene sulfonate can be used to study various cell membranes. See, for example, T. A. Pederson and A. Lode, Arch. Mikrobiol. 77, 118-126 (1971); ); W. A. Cramer and S. K. Phillips, J. Bacteriol., 104(2), 819-825 (1970); and R. B. Freedman et al., Probes Struct. Funct. Macromol. Membranes, Proc. Colloq. Johnson Res. Found., 5th 1969 (Pub. 1971), 1, 325-338 (Eng.). We are unaware, however, of any disclosure which makes use of such probes to determine whether a given microbe has gram positive or gram negative properties.

Quite surprisingly, we have found that differences in cell wall lipid amounts can be used to distinguish gram positive and gram negative organisms. Our method avoids many of the problems associated with present gram stain methods. Details of our method and devices for using it are disclosed herein.

SUMMARY OF INVENTION

The microbial culture apparatus for determining whether an unknown organism has gram positive or gram negative properties comprises microbial growth medium retention means containing microbial growth medium having incorporated therein a lipophilic fluorescent material in an amount sufficient to permit fluorometric detection of microbes grown on the medium, the growth medium retention means having associated therewith means for localizing and identifying a colony of an unknown microbe, and a known gram positive microbe and/or a known gram negative microbe. The method of determining whether the unknown organism has gram positive or gram negative properties comprises the steps of culturing an unknown organism on a growth medium containing the lipophilic fluorescent material in an amount sufficient to permit fluorometric detection of the cultured organisms and then comparing the fluorescent properties (quantity of fluorescence) of that organism with the fluorescent properties of similarly cultured gram positive and/or gram negative organisms.

In one preferred embodiment, fluorometric determinations are made with aqueous suspensions of the organisms. In another embodiment, the fluorescence of the unknown is compared with previously prepared gram stain identification means (e.g. cards spotted with varying amounts of fluorescent dye). One of our preferred lipophilic fluorescent materials is 8-anilino-1-naphthalene sulfonic acid (ANS) or a salt thereof. A preferred growth medium is a gel-like nutrient (e.g. agar).

SPECIFIC EMBODIMENTS

Figure 1:
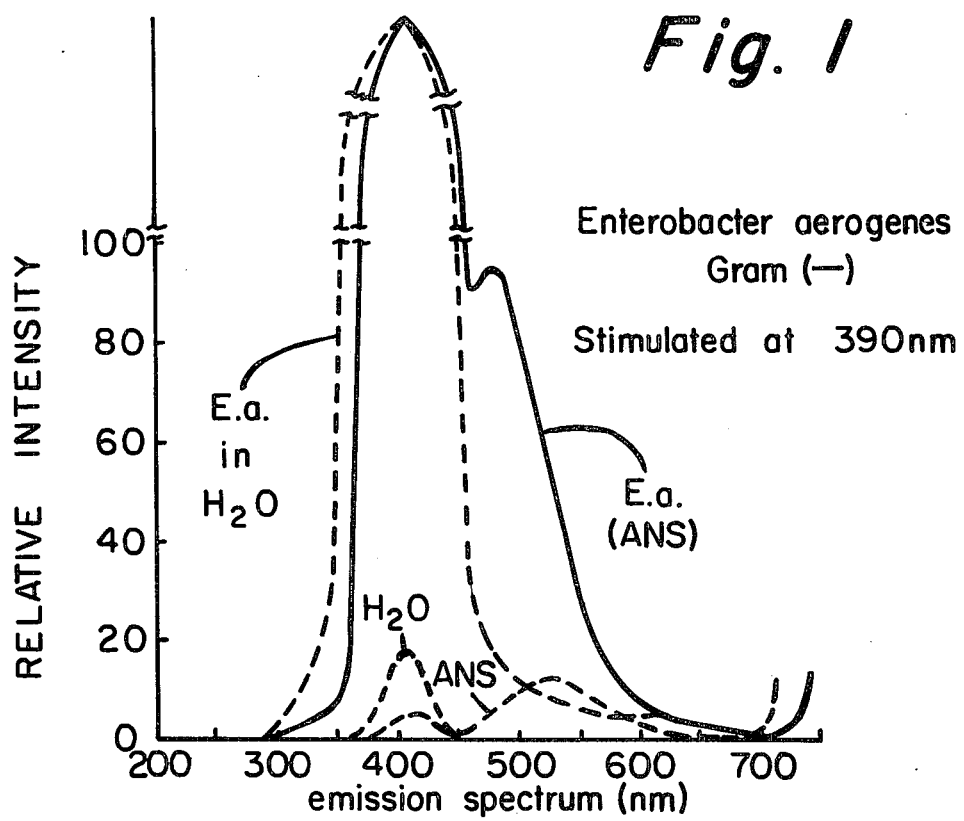
FIG. 1 illustrates a comparison of the spectrophotofluorometric emissions of a known gram negative organism grown on an ANS-containing growth medium, the organism in water, water, and ANS in water.

Our discovery is based in part on earlier observations (disclosed in related application Ser. No. 701,894 now U.S. Pat. No. 4,049,499)that certain fluorescent materials such as 8-anilino-1-naphthalene sulfonic acid (ANS), when incorporated into growth medium, allowed the fluorometric detection of bacterial colonies. In the work that led to the above observations, it was found that ANS did not inhibit the growth of gram positive or gram negative microbes. In subsequent work, however, we found observable differences in fluorescence produced by each type of microbe. All other conditions being identical, it was found that gram negative bacteria fluoresced more than gram positive bacteria grown on an ANS-containing growth medium (agar). It occurred to us that such differences might reflect differences in quantum efficiencies in wavelengths of emitted light from each bacterial type and also be based on differences in cell wall constituents, especially lipid content. To our surprise, it was found that a lipophilic marker could be used to distinguish gram positive and gram negative microbes.

Since our method of distinguishing the two classes of microbes appears to be based on differences in lipid content of the cell walls of the organisms, it is thought that a variety of lipophilic markers may be incorporated into a given microbial growth medium. As an unknown colony grows, the higher lipid content of gram negative organisms will tend to concentrate a lipophilic marker more than at those colonies composed of cells having a lower lipid content in their cell walls. The ultimate determination of whether an unknown specimen is gram positive or gram negative is made by simply quantitating the given marker vis-a-vis given standards for that marker. The amount of lipophilic marker in a given growth medium need only be sufficient to be detectable by some means.

As a very practical matter, we have found that lipophilic fluorescent materials make ideal markers, especially since they can be used to differentiate very small differences in amounts of fluorescent materials. Such small differences might exist in cases where a gram negative sample microbe has a relatively small lipid amount or a gram positive microbe has a relatively large lipid quantity in its cell wall. Further, since relative amounts of fluorescence can be determined optically with a high degree of precision and reliability, a variety of standards can be used to determine whether an unknown (unk.) organism has gram negative (−) or gram positive (+) properties.

As used herein, the expression microbe or its equivalent refers to any unicellular organism and includes, but is not limited to, bacteria and other organisms which can be distinguished on the basis of gram staining techniques. Media that can be used according to the disclosures herein include any materials (e.g. agar, fluids, etc.) upon which or in which microbes can be incubated and grown. Incubating conditions refers to those conditions recognized as being conducive to the growth of microbes and include a variety of conditions (e.g. time, temperature, pH, etc.). Lipophilic fluorescent materials includes any material which is generally lipophilic, relatively non-inhibiting to the growth of microbes, and detectably fluorescent in a non-polar environment by visual or optical means. It can be appreciated that a large number of fluorescent materials meet the above requirements. Among the compounds found useful were the sodium and magnesium salts of ANS, 8-p-toluidino-1-naphthalene sulfonic acid, 6-p-toluidino-2-naphthalene sulfonic acid, acridine orange, and 1-pyrenebutyric acid.

It should be noted that since the higher lipid content of the cell wall of a microbe having gram negative properties tends to concentrate the lipophilic fluorescent material at the locus of the growing colony, some amount of fluorescence is tolerable in the medium itself. For example, since the determining factor is cell wall lipid content, varying degrees of lipophilicity can be tolerated in the fluorescent marker material or even the growth medium. Thus, when incorporated into an appropriate microbial growth medium, the marker need only have a tendency to be more lipophilic than lipophobic. It should also be noted that, in principle, the method disclosed herein can be based on determining the relative fluorescence of a lipophobic marker when that same marker is used in a medium for known positive or known negative microbes. Hence the expression lipophilic, when applied to the methods and materials disclosed herein, is used to denote a relative state of lipophilicity which can be used to advantageously exploit the known differences in cell wall constituents of gram positive and gram negative microbes.

Of the lipophilic, fluorescent, non-inhibiting materials used to date, ANS salts (collectively referred to as ANS) gave excellent results in determining whether a given microbe had gram positive or gram negative properties. The use of this material is illustrated in the examples below.

EXAMPLES 5 gram positive and 12 gram negative species of bacteria were separately streaked on nutrient agar (Difco) and on the same nutrient agar having incorporated therein about 0.08 mg/ml of ANS (magnesium salt), all contained in Petri plates. These cultures were incubated overnight at 37° C. At this time, all colonies on the ANS plates fluoresced when visually observed with predominantly 366 nm illumination. In the case of colonies grown on the plates containing no ANS, only the *Pseudomonas aeruginosa* colonies fluoresced to any noticeable degree. That species, however, is known to produce a fluorescent pigment. See, for example, Buchanan, R. E. and Gibbons, N. E., Bergey's Manual of Determinative Bacteriology, 8th Ed., pp. 221-222, Williams and Wilkins Co., Baltimore, 1974. In each case the amount of bacterial growth in the presence and absence of the ANS was similar.

Growth from the plates was removed and suspensions of optical density at 590 nm of 1.0 were made using water for the nutrient agar plates and a water solution of ANS at 0.08 mg/ml for the ANS plates. The emission spectra of these suspensions, the water, and ANS were then determined using an American Instruments Spectrophotofluorometer. Spectra were determined using stimulating light at 350, 370, 390, and 410 nm. The maximum fluorescence was obtained at 390 nm stimulation. To our surprise, it was found that the all gram negative organisms tested had a considerably higher degree of relative fluorescence than the gram positive samples when suspensions of both were tested for relative fluorescence at 480 nm after stimulation at 390 nm. The observed differences in relative fluorescence for each species tested are summarized in the table.

TABLE

Bacteria Tested For Relative Fluorescence at 480 nm After Stimulation With Light At 390 nm

| | Relative Fluorescence |
|---|---|
| GRAM NEGATIVE | |
| *Acinetobacter anitratum* | 126 |
| *Arizona sp.* | 148 |
| *Rhodospirillum rubrum* | 98 |
| *Proteus mirabilis* | 325 |
| *Klebsiella sp.* | 345 |
| *Citrobacter sp.* | 166 |
| *Pseudomonas testosteroni* | 270 |
| *Pseudomonas aeruginosa* | 128 |
| *Serratia marcescens* | 160 |
| *Proteus vulgaris* | 79 |
| *Escherichia coli* | 51 |
| *Enterobacter aerogenes* | 87 |
| GRAM POSITIVE | |
| *Corynebacterium sp.* | 24 |
| *Arthrobacter sp.* | 19 |
| *Bacillus subtilis* | 23 |
| *Bacillus globigii* | 8 |
| *Staphylococcus sp.* | 9 |

Figure 2:
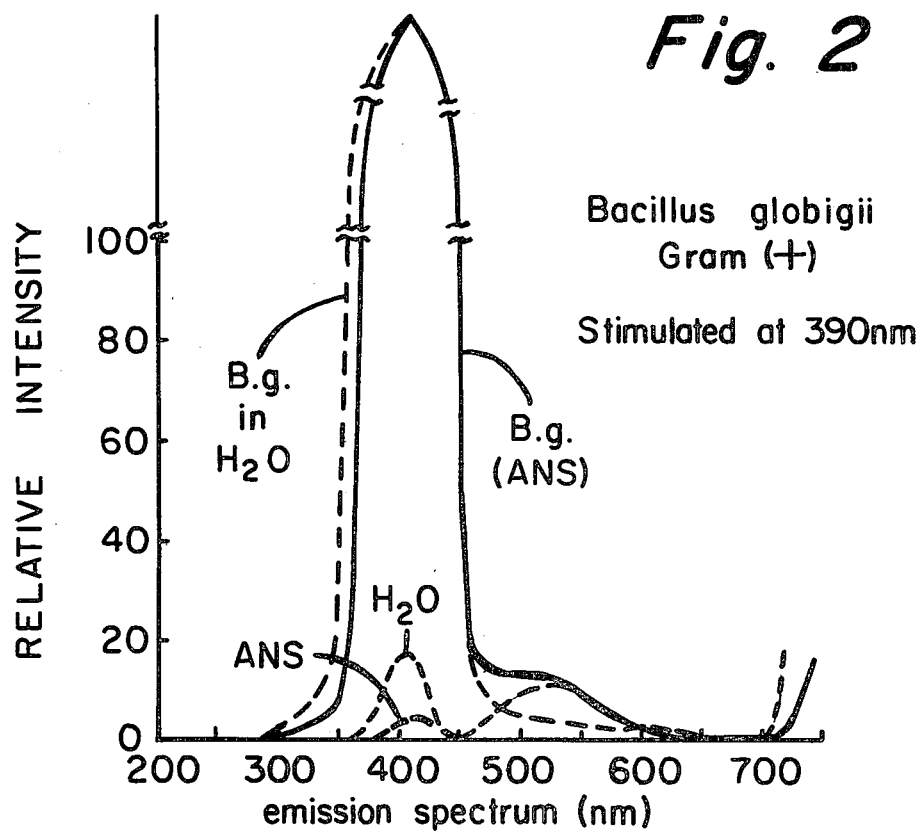
FIG. 2 illustrates a similar comparison made with a known gram positive organism.

Representative spectrophotofluorometric scans of a known gram negative microbe (*Enterobacter aerogenes*) are shown in FIG. 1. Scans of a known gram positive microbe (*Bacillus globigii*) are shown in FIG. 2. In all bacterial suspensions, there was a large light scattering peak centered on the wavelength of the stimulating light. In the gram negative ANS suspension (FIG. 1) there also was a large degree of fluorescence in the region from about 460 to 600 nm with a distinct peak at approximately 480 nm. Comparison of the water suspension, water alone, and the ANS curves in FIG. 1 with the ANS bacteria curve confirms that the observed fluorescence is due to interaction between the bacteria and the ANS. Similar conclusions may be drawn from FIG. 2 except that it can be noted that the total amount of fluorescence is much less than that found with the gram negative organisms and is found in the region of about 460 to 600 nm but without a definite peak being formed, although in some cases, there is a very broad peak at about 510 nm.

As can be seen from the Table, which summarizes the results of similar observations, the gram negative relative fluorescence ranged from 51 to 345 with an average of 165. The gram positive relative fluorescences ranged from 8 to 24 with an average of 17.

It is clear from the above results that the gram negative microbes, when grown on the lipophilic fluorescent ANS containing medium, fluoresce significantly more than similarly cultured gram positive species, thus permitting a relatively simple and quick method for distinguishing the two or determining whether an unknown organism has gram negative or gram positive properties. As noted above the lipophilic, fluorescent markers may be incorporated into the medium in the form of their common or commercially available salts (e.g. magnesium, sodium, etc.). The medium used may be any microbe culture (growth) medium on which both types of organisms can grow (e.g. agar, etc.). The amount of marker or salt thereof in the medium need only be an amount sufficient to permit the fluorometric detection of the microbes without deleterious effects on microbe growth. As a practical matter, in the case of ANS, a range of about 0.08 to 0.5 mg/ml of ANS to medium is preferred.

Figure 3:
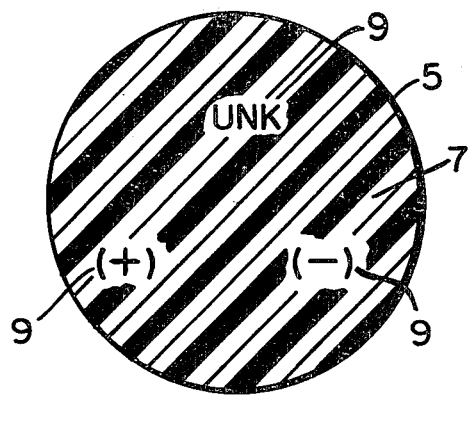
FIGS. 3-5 illustrate various embodiments of the culturing devices which may be used to accomplish the methods disclosed herein.
Figure 4:
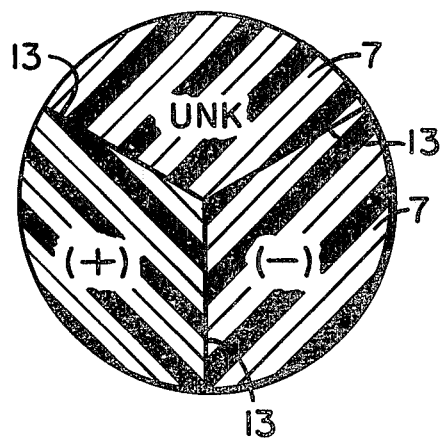
Figure 5:
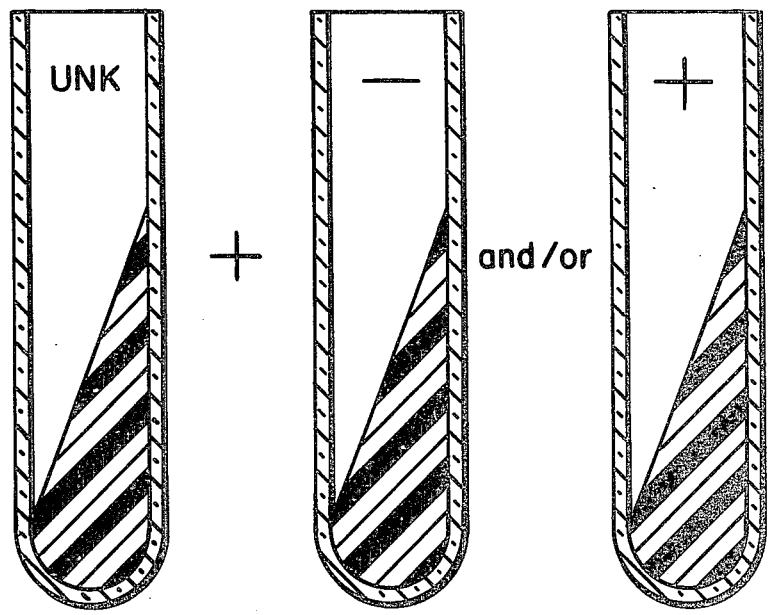

As illustrated in FIGS. 3–5, the ANS-medium may be contained in devices having various configurations and microbe locating and identifying means for facilitating the gram property determination. For example, FIG. 3 illustrates a simple petri dish 5 containing the medium 7 (e.g. 25 ml of agar containing about 0.08 mg/ml ANS). The dish and contained medium have means for localizing and referencing the growth of known gram positive, known gram negative and unknown organisms. In FIG. 3, the culture localizing and referencing means 9 are simply areas on the medium for streaking the organisms and identified by means such as embossed "+", "−" and "UNK" for the sample positioned at the container bottom. For convenience and assurance in localizing the cultures, the growth areas may be separated by walls 13 which can be an integral part of the dish 5 or removable inserts. See FIG. 4. Alternatively, the separate growth areas may be separate dishes, tubes (FIG. 5) etc., which can be conveniently labeled to indicate the culture to be grown thereon. For optimum sensitivity, the known gram negative sample should yield the least fluorescent colonies and the known gram positive sample should yield the most fluorescent colonies, thus making it easier to determine which reference sample the unknown resembles in quantity of fluorescence. For example, based on the relative fluorescence results of the above table, the *E. coli*, having the least fluorescence for a gram negative microbe, could be used as a standard. Alternatively, the most fluorescent gram positive microbe of the table, *Corynebacterium sp.*, could also be used as a standard. In some cases, only one such standard will be needed to determine if an unknown is positive or negative. Given this disclosure, it will become apparent to those skilled in the art that numerous variations for determining the best standard or standards and the best configuration of the culture device or devices are possible, depending on such factors as convenience, material availability, economics, etc.

For example, beside simply using a divided plate as described above, the unknown sample can be incubated on the medium and the resulting fluorescence can be compared with reference cards showing similar fluorescences of known reference microbes. One spot having a relatively low fluorescence could correspond to a gram positive species whereas a highly fluorescent marking would correspond to a gram negative microbe, thus facilitating correlation of the unknown fluorescence. Another alternative would take advantage of the observed differences in the color (fluorescence) of emitted light. Since gram positive and gram negative groups emit different colors of fluorescence, the unknown color could be compared with gram positive and negative control colors. A further alternative would involve arbitrarily classifying the amount of fluorescence of an unknown according to a system (e.g. numerical system) related to known results. It should be noted that the methods disclosed herein can also be used to determine the lipid content of a given microbe relative to the lipid content of the cell walls of a given standard (reference) microbe. Alternatively, the disclosed methodology can be used to detect contamination of cultures of gram negative bacteria with gram positive microbes or vice-versa. Other identification methods will occur to those having a need to identify organisms or cell wall constituents.

Accordingly, it is intended that the specific examples given above should be construed as illustrative only, and that the scope of the invention disclosed herein should be limited only be the claims.

We claim:

1. A method of determining the gram staining properties of a microbe, the method comprising the steps of:
   (a) incubating a sample of the microbe on a microbial culture medium having incorporated therein a lipophilic fluorescent material in an amount sufficient to permit the fluorometric detection of microbial growth;
   (b) determining the quantity of fluorescence of the incubated microbe; and
   (c) comparing the quantity of fluorescence of the incubated microbial sample with the quantity of fluorescence of similarly incubated microbe known to be a gram positive or a gram negative microbe.

2. The method of claim 1 wherein the microbial culture medium used in step (a) comprises a gel-like material.

3. The method of claim 2 wherein the medium comprises an agar.

4. The method of claim 1 wherein the lipophilic fluorescent material comprises 8-anilino-1-naphthalene sulfonic acid or a salt thereof.

5. The method of claim 1 wherein the lipophilic fluorescent material comprises 8-p-toluidino-1-naphthalene sulfonic acid or a salt thereof.

6. The method of claim 1 wherein the lipophilic fluorescent material comprises 6-p-toluidino-1-naphthalene sulfonic acid or a salt thereof.

7. The method of claim 1 wherein the lipophilic fluorescent material comprises acridine orange.

8. The method of claim 1 wherein the lipophilic fluorescent material comprises 1-pyrenebutyric acid or a salt thereof.

9. The method of claim 1 wherein the microbial culture medium comprises an agar and the lipophilic fluorescent material is 8-anilino-1-naphthalene-sulfonic acid in an amount ranging from about 0.08 to 0.5 mg/ml of agar.

10. The method of claim 1 wherein the fluorescence quantity of step (b) is determined using an aqueous suspension of the incubated sample.

11. A method of determining whether the lipid content of the cell wall of a given microbe is above or below the lipid content of the cell wall of a microbe used as a reference, the method comprising the steps of:
    (a) incubating the given microbe on a microbial growth medium having incorporated therein a lipophilic fluorescent material in an amount sufficient to permit the fluorometric detection of microbial growth;
    (b) determining the quantity of fluorescence of the incubated microbe; and
    (c) comparing the quantity of fluorescence of step (b) with the quantity of fluorescence emitted by the reference microbe when incubated according to step (a).

12. The method of claim 11 wherein the reference microbe is a gram negative microbe.

13. The method of claim 11 wherein the reference microbe is a gram positive microbe.

14. The method of claim 11 wherein the microbial growth medium comprises a fluid.

15. The method of claim 11 wherein the microbial growth medium comprises gel-like material.

16. The method of claim 15 wherein the growth medium comprises an agar.

17. The method of claim 11 wherein the lipophilic fluorescent material comprises 8-anilino-1-naphthalene sulfonic acid or a salt thereof.

18. The method of claim 11 wherein the lipophilic fluorescent material comprises 8-p-toluidino-1-naphthalene sulfonic acid or a salt thereof.

19. The method of claim 11 wherein the lipophilic fluorescent material comprises 6-p-toluidino-2-naphthalene sulfonic acid or a salt thereof.

20. The method of claim 11 wherein the lipophilic fluorescent material comprises acridine orange.

21. The method of claim 11 wherein the lipophilic fluorescent material comprises 1-pyrenebutyric acid or a salt thereof.

22. The method of claim 11 wherein the microbial growth medium comprises agar and the lipophilic fluorescent material is 8-anilino-1-naphthalene sulfonic acid or a salt thereof in an amount ranging from about 0.08 to 0.5 mg per ml of agar.

* * * * *